United States Patent [19]
Rippon et al.

[11] Patent Number: 5,496,379
[45] Date of Patent: Mar. 5, 1996

[54] DYEING PROCESS FOR KERATIN MATERIALS, WITH IMPROVED EXHAUSTION OF BATH CONSTITUENTS

[75] Inventors: John A. Rippon, Torquay; Francis J. Harrigan, Highton, both of Australia

[73] Assignee: Commonwealth Scientific and Industrial Research Organisation, Australia Capital Territory, Australia

[21] Appl. No.: 284,426

[22] PCT Filed: Feb. 3, 1993

[86] PCT No.: PCT/AU93/00045

§ 371 Date: Nov. 9, 1994

§ 102(e) Date: Nov. 9, 1994

[87] PCT Pub. No.: WO93/15259

PCT Pub. Date: Aug. 5, 1993

[30] Foreign Application Priority Data

Feb. 4, 1992 [AU] Australia .................. PL 0673
Oct. 15, 1992 [AU] Australia .................. PL 5373

[51] Int. Cl.$^6$ .................. D06P 3/14; D06P 1/62; D06P 1/607
[52] U.S. Cl. .................. 8/490; 8/576; 8/606; 8/128.1; 8/128.3; 8/917
[58] Field of Search .................. 8/128.1, 128.3, 8/917, 490, 606, 576; 562/107

[56] References Cited

U.S. PATENT DOCUMENTS

| | | | |
|---|---|---|---|
| 3,686,411 | 8/1972 | Frick et al. | 424/273 |
| 4,063,877 | 12/1977 | Elliot et al. | 8/913 X |
| 5,057,539 | 10/1991 | Neukom et al. | 514/531 |
| 5,358,967 | 10/1994 | Carlson | 514/615 |

FOREIGN PATENT DOCUMENTS 8100 2/1974 Japan.

WO88/07602 10/1988 WIPO.

OTHER PUBLICATIONS

Harrigan et al, Proceedings, The Textile Institute 1988 Annual World Conference, pp. 412–419.

Rippon et al, Proceedings of the Eighth International Wool Textile Research Conference, Feb. 1990, vol. IV, pp. 50–59.

*Primary Examiner*—Margaret Einsmann
*Attorney, Agent, or Firm*—Sughrue, Mion, Zinn, Macpeak & Seas

[57] ABSTRACT

A method of applying dye to keratin fibres comprises pretreating the fibres by contacting them with an alkaline solution of an amphoteric surfactant, and thereafter applying dye to the pretreated fibres from a dyeing solution substantially deficient of surfactant-type levelling agents. Also disclosed is a novel surfactant compound comprising an alkoxylated hydroxysulphobetaine of formula:

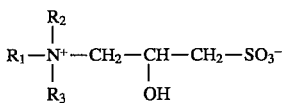

where:
  $R_1$ is a hydrocarbon group selected from the range $C_{12}H_{25}$ up to $C_{21}H_{43}$; and
  $R_2$ and $R_3$ are poly(alkylene oxide) groups, each having $n$ alkylene oxide units, where $3 \leq n \leq 21$.

In another aspect, there is disclosed a method of applying dye to keratin fibres comprising contacting the fibres with a bath liquor comprising an alkaline solution of the above surfactant, and thereafter adding dye to the bath liquor and applying the dye to the fibres from the bath liquor.

42 Claims, No Drawings

DYEING PROCESS FOR KERATIN MATERIALS, WITH IMPROVED EXHAUSTION OF BATH CONSTITUENTS

The present invention relates to the dyeing of keratin fibres, and has particular though not exclusive application to the dyeing of tippy wool. In a preferred aspect, the invention relates to improvements in the equilibrium exhaustion of insectproofing agents added to dye baths, compared with the levels obtained by existing methods. The invention is primarily concerned with wet dyeing processes which utilise water soluble dyest as distinct from, e.g. water dispersible dyes. In a particular aspect, the invention provides a novel surfactant compound having utility in the treatment of keratin fibres prior to dyeing.

Wool and other keratinous fibres are usually dyed by exhaustion methods from acidic liquors: the liquors often contain various reagents in addition to dyes. The purpose of these reagents is to control the manner in which dyes are sorbed by the fibres and hence to control the evenness of the final dyeing. These compounds, collectively referred to as "levelling agents", may be inorganic salts such as sodium sulphate, but for many wool dyes, various types of surfactants are more effective as levelling agents. Anionic, cationic or amphoteric surfactants are commonly used, either alone or in blends, for dyeing wool by exhaustion methods. The mode of action of these levelling agents, especially the surfactants, usually involves formation of a complex with the dye. The complex is sorbed more evenly by the wool than the dye alone.

Improved evenness of dye sorption is particularly important when dyeing tippy wool in order to avoid a skittery appearance in the final product, and thus surfactant levelling agents are generally employed when dyeing tippy wool. Tippy wool is wool damaged by weathering to such an extent that the tip and root portions of fibres have markedly different dyeing properties. "Skittery" is a term used to describe an undesired speckled effect arising from differences in colour between adjacent fibres or portions of the same, an effect often associated with dyeing tippy wools.

Although the dye/surfactant complex improves evenness of dye sorption, formation of the complex can lead to a decrease in the equilibrium exhaustion of the dye; this is wasteful of dyestuff and causes possible effluent disposal problems. The latter is a particular problem for dyestuffs containing heavy metal atoms, for example chromium, cobalt or copper.

Another possible problem in wool dyeing that can result from the presence of surfactant-type levelling agents in the dyebath involves the application of chemicals that prevent damage of wool products by insects, e.g. moths, during storage or use. Such insect-proofing agents are often applied to wool by exhaustion methods. The agents can be applied in a separate operation to the dyeing procedure; however, it is common practice to add these agents to the dyebath, so that they are applied to the wool simultaneously with dyes. In cases where a surfactant-type levelling agent is present in the dyebath to improve the quality of the dyerag, an adverse effect is often obtained with respect to the uptake of insect-proofing agent by the wool. (See for example Zimmerman, M. and Höcker, H., Studies on moth-proofing of wool with permethrin, Milliand Textilberichte, 69 (1988), p. 909). This effect is analogous to the aforementioned effect of many levelling agents on the exhaustion of dyestuffs. An undesirable consequence of a reduction in the exhaustion of insect-proofing agents from dyebaths is that effluents discharged from the premises where the treatments are carried out may contain mounts of the insect-proofing agents that are harmful to the environment.

International patent publication WO88/07602 (application PCT/AU88/00086) discloses a process for improving dyestuff exhaustion under milder dyebath conditions than conventionally employed. The process involves an aqueous pre-treatment of keratin fibres such as wool with an amphoteric surfactant under alkaline conditions, prior to and quite separately of the dye treatment. It has now been surprisingly found that such a pre-treatment permits improved dyeing properties without the necessity to add conventional surfactant levelling agents to the dyebath. In particular, the improvements in dyeing properties relate to excellent levelling and coverage of tippiness compared with untreated material, despite the substantial absence of levelling agents, together with very high degrees of exhaustion of dyes achievable in the absence of the levelling agents. It is moreover found that, when insect-proofing agents are added to the dyebath, the improved dyelag properties are obtained together with good exhaustion of insect-proofing agents, when these are applied simultaneously with the dyestuffs.

It has been still further surprisingly found that by suitable selection of the amphoteric surfactant for the alkaline solution, the pretreatment and dyeing steps can be effected in succession from a single bath liquor, with appropriate conversion of the liquor between the steps.

The invention therefore provides, in a first aspect, a method of applying dye to keratin fibres comprising pretreating the fibres by contacting them with an alkaline solution of an amphoteric surfactant, and thereafter applying dye to the pretreated fibres from a dyeing solution substantially deficient of surfactant-type levelling agents.

By "substantially deficient" is meant herein that the dyebath does not contain surfactant-type levelling agents at all or, if it does, that the concentration of the levelling agents is substantially less than conventionally employed in a dyebath of the kind used to dye the fibres.

Most preferably, the dyeing solution is aqueous and contains water-soluble dye. The dyeing solution is also preferably acidic.

The invention also affords, in a second aspect, a method of applying dye to keratin fibres, wherein the dye is applied from a dyeing solution substantially deficient of levelling agents, to fibres which have been pretreated by contacting them with an alkaline solution of an amphoteric surfactant.

As extremely low concentrations of surfactant can improve dyeing properties of the fibres, there is no absolute lower limit for the amount of surfactant which needs to be used in the pre-treatment. However, for optimum results it is preferred that the weight of surfactant is at least equal to 0.1% oww (i.e. on weight wool) with respect to the fibres being treated.

The amphoteric surfactants used for the purposes of the pre-treatment of the present invention may contain a variety of cationic and anionic groups. The preferred type of cationic groups are amine salt, quaternary nitrogen, pyridinium or substituted imidazoline groups and the anionic groups are carboxyl, sulphate ester, thiosulphate, sulphonic acid or phosphate moieties. The amphoteric reagents can contain more than one type of cationic and/or anionic group; they may also contain other types of groupings that are neutral in character, for example hydrocarbon or alkylene oxide chains.

Particularly useful are the following types of amphoteric surfactants:

(a) N-alkyl betaines and sulphobetaines of the type:

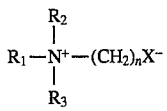

where $R_1$, $R_2$ and $R_3$ are alkyl groups; $n \geq 1$; $X^-$ is either $-COO^-$ or $-SO_3^-$ (b) Alkyl-amide betaines and sulphobetaines of the type:

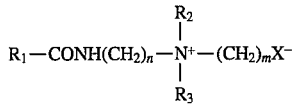

where $R_1$, $R_2$ and $R_3$ are alkyl groups: $m \geq 1$; $n \geq 1$ $X^-$ is either $-COO^-$ or $-SO_3^-$ (c) Amphoteric surfactants of the following type:

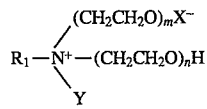

where:

$R_1$ is an alkyl group, usually containing less than 22 carbon atoms.

m and n are integers usually between 1 and 30.

$X^-$ is $-COO^-$; $-SO_3^-$; $-OSO_3^-$; $-SSO_3^-$; or $HPO_4^-$

Y is an amide or other fatty acid derivative.

(d) Amphoteric surfactants of the following type:

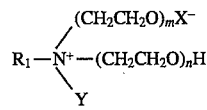

where:

$R_1$ is an alkyl group, usually containing less than 22 carbon atoms.

m and n are integers, usually between 1 and 30.

$X^-$ is $-COO^-$; $-SO_3^-$; $-SSO_3^-$; or $HPO_4^-$

Y is a substituted or unsubstituted alkyl group, usually containing less than five carbon atoms.

(e) Amphoteric surfactants of the following type:

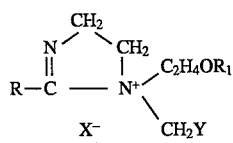

where:

R is a fatty acid radical.

$R_1$ is H, Na or $CH_2$ COOM.

X is OH, an acid salt or the salt of an anionic surface active sulphate or sulphonate.

Y is COOM, $CH_2COOM$ or

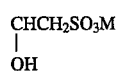

M is Na, H or an organic base.

Alternatively, it has been found that a particularly effective class of amphoteric surfactant for the purposes of the invention comprises a novel class of compounds in accordance with a third aspect of the invention. In this aspect, the invention provides a surfactant compound comprising an alkoxylated hydroxysulphobetaine of formula:

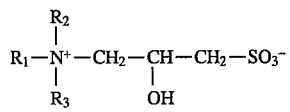

where:

$R_1$ is a hydrocarbon group selected from the range $C_{12}H_{25}$ up to $C_{21}H_{43}$; and $R_2$ and $R_3$ are poly (alkylene oxide) groups, each having n alkylene oxide units, where $3 \leq n \leq 21$.

Preferably, $R_2$ and $R_3$ are each polyethylene or polypropylene oxide groups or a mixture of polyethylene and polypropylene oxide units.

Most preferably, $R_2$ and $R_3$ respectively contains $n_1$ and $n_2$ alkylene oxide units and $3 \leq n_1 + n_2 \leq 21$ In the process of the first and second aspects of the invention, the mount of surfactant required depends upon the percentage of the active constituent in the product; however, in general, this is in the range 0.1–20 g/l, when applied at a liquor ratio of 30:1.

As discussed above, the pretreatment is carried out under alkaline conditions. The most suitable pH values are in the range greater than 7 but not more than 11. The pH value of the pretreatment liquor can be set by any convenient method, using organic or inorganic reagents, or mixtures of these. It is convenient, although not essential, to use a buffered system because this ensures that the maximum degree of reproducibility of the effect is obtained. A particularly useful pretreatment pH is in the range pH 8 to 8.5, because this provides the optimum improvements in dyeing properties whilst minimising the possibility of alkaline degradation of the fibre.

The treatment can be carried out at any temperature in the range 5° to 100° C. Temperatures that are particularly suitable are those commonly used for scouring wool, viz 20° to 50° C. Although any treatment time from one minute to several hours can be used, times of 10 to 60 minutes are particularly suitable.

An advantage of the process is that the treatment can be included in the normal sequence of wool processing. For example, as a pretreatment prior to the dyeing of loose stock, silver, top, yarn, fabric or garments. The treatment can also be applied as part of the final stages of raw wool scouring.

According to some embodiments of the invention, the liquor is discarded and the wool dyed from a fresh bath. The material may be rinsed before dyeing, but this is not essential. The treated material can be dyed immediately, or dried and dyed at some later time, without any loss of the effect.

According to an alternative embodiment, said pretreatment and said dye applying steps are effected in a single bath liquor which is initially an alkaline solution for said pretreatment step and then converted to said dyeing solution for the dye applying step, said amphoteric surfactant being selected so as to be substantially exhausted from the bath before said conversion of the bath. In general, a suitable range of amphoteric surfactants for this purpose is thought to be those with alkoxyl chains having between 3 and 21 units, most preferably in the range 7 to 15. An especially suitable amphoteric surfactant for this purpose is a surfactant selected from the class of compounds comprising the third aspect of the invention.

Accordingly, in a fourth aspect of the invention, there is provided a method of applying dye to keratin fibres comprising contacting the fibres with a bath liquor comprising an alkaline solution of an amphoteric surfactant, and thereafter adding dye to the bath liquor and applying the dye to the fibres from the bath liquor, wherein said amphoteric surfactant comprises an alkoxylated hydroxysulphobetaine of formula:

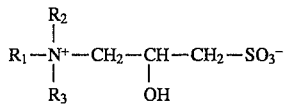

where:
R$_1$ is a hydrocarbon group selected from the range $C_{12}H_{25}$ up to $C_{21}H_{43}$;

R$_2$ and R$_3$ are poly (alkylene oxide) groups, each having n alkylene oxide units, where $3 \leq n \leq 21$;

and wherein said bath liquor is substantially deficient of any surfactant-type levelling agents other than said alkoxylated hydroxysulphobetaine.

Preferably, after the contacting of the fibres with the alkaline bath liquor, and before the dye is added, the bath liquor is converted from an alkaline solution to an acidic solution.

The surprising observation has been made with this fourth aspect of the invention that excellent coverage of tippiness can be obtained, without retardation of the inset-proofing agent, e.g. the synthetic-pyrethroid, permethrin, added to the dyebath. This finding is in striking contrast to the effects found with existing, commercially available, surfactant-type dye levelling agents. With these products, at the concentrations required to give good coverage of tippiness, a marked retardation of exhaustion of permethrin onto the wool occurs. Thus, the one-bath method is torque in that it enables the benefits of a dye levelling agent to be obtained, without a concomitant reduction in uptake by wool of insect-proofing agent. This observation has important environmental consequences, because of possible toxic effects to aquatic life of high concentrations of permethrin in effluent liquors discharged from wool dyehouses.

It is thought that the one-bath embodiment may be effective because the selected amphoteric surfactants are more readily taken up by the fibres, and thus the surfactants are effective for the pretreatment step without requiring effective concentrations which leave significant residual surfactant. It may be necessary for the concentration of the amphoteric surfactant to be selected so that it is substantially wholly taken up by the fibres, whereby the bath liquor is made substantially deficient of residual surfactant before dye is added to the liquor.

In the one-bath procedure, both the pretreatment and dyeing steps are carried out from the same liquor. Thus in one embodiment according to the fourth aspect of the invention, the one-bath method consists of the following steps:

(a) the wool is treated with the amphoteric reagent under alkaline conditions (pH preferably greater than 7, not greater than 11, e.g. 8);

(b) the liquor is adjusted to an acidic pH (pH preferably less than 7, not less than 3, e.g. 4.5);

(c) dyes and insect-proofing agent (e.g. permethrin) are added;

(d) the dyebath is heated to an equilibrium temperature (usually 85° to 100° C.), where it is held for the required time to effect dyeing;

(e) the liquor is discarded and the wool is rinsed.

In the one-bath method, it is important that an excessive amount of the amphoteric surfactant is not used, otherwise retardation of uptake of dyes and insect-proofing agent will occur. However, as emphasised above, it was surprising that a large improvement in the coverage of tippiness was found with a (low) concentration of the surfactant that did not suppress the uptake of insect-proofing agent e.g. permethrin. It has been found that the amount of the 50% active product added to the liquor should not exceed 0.2% oww when used at a liquor ratio of 10:1 or less or 0.4% oww at a liquor:wool ratio greater than 10:1.

In any of the aforementioned aspects of the invention, all classes of dyes used for the colouration of keratin fibres may be used: e.g. acid levelling, acid milling, 1:1 premetallised, 1:2 premetallised, chrome, and reactive dyes.

Wool dyes typically require an acid bath and the dyebath may then be set by adjusting the pH to the required value less than 7 by addition of an acid, the particular acid being determined by the class of dye to be applied. In certain cases, inorganic salts, such as sodium sulphate, or other reagents that do not interfere with the exhaustion of the dyes may also be added to the dyebath. Examples of such reagents are anti-foaming agents and dye dispersing agents, such as sodium naphthalene sulphonates, lignosulphonates or certain poly (alkylene oxide) derivatives. Insect-proofing, e.g. moth-proofing, agents may also be added, when required.

After the dyebath is set, dyeing may be carried out by increasing the temperature to the required value, where it is maintained for the required time. Although temperatures in the range 70° to 110° C. may be used, particularly suitable dyeing temperatures are those between 75° C. and 100° C.

The keratin fibres that can be treated will normally be new or reprocessed wool from sheep. This can include wool that has been modified, for example, by a shrink-resist or other treatment. The keratin fibres may, however, also be derived from the following sources: alpaca, angora, cashmere, mohair, vicuna, guanaco, rabbit, camel, llama or human hair; or blends of these fibres with the wool from sheep. The material may consist wholly of keratinous fibres, or of blends with synthetic fibrous and filamentary material, or with natural or regenerated cellulosic fibres, or with other natural fibres, in particular silk.

The aforementioned alkoxylated hydroxysulphobetaines, comprising the third aspect of the invention and utilised in the method of the fourth aspect, may be prepared by reacting epichlorohydrin (2,3epoxy-1-chloropropane) with an alkoxylated amine for several hours in a mixture of propane diol and water, then adding sodium sulphite and continuing the reaction for several more hours at a higher temperature.

The invention is illustrated by the following examples.

EXAMPLE 1

A woven, wool worsted fabric (25 g) was treated at a liquor:goods ratio of 20:1, for 30 minutes at 40° C. with a solution containing 0.5 grams per liter of the compound of the formula.

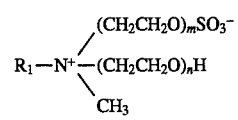

where R is the hydrocarbon radical of tallow fatty amine, and m+n=8.

The solution was adjusted to pH 8 to 8.5 with a mixture of sodium carbonate and sodium bicarbonate.

Following treatment, the liquor was discarded and the sample was subsequently dyed from a fresh bath, at a liquor:goods ratio of 20:1, initially to 40° C. and set to pH 4.5 with formic acid. After addition of a solution containing the following dyes, 0.175% oww. Neutrichrome Grey SBG and 0.059% oww Neutrichrome Bordeaux S3B, the dyebath was heated to 90° C. over 25 minutes. The dyeing time at 90° C. was 30 minutes, after which the bath was cooled to 75° C. The sample was then rinsed, and dried. The dyebath was completely exhausted and, furthermore, no dyestuff was removed on rinsing. The sample was evenly dyed and was free from skitteriness.

A sample of the wool fabric was also dyed, with the mixture of dyes described above, by the following conventional procedure. The dyebath, was set at 40° C. to pH 4.5 with acetic acid. A levelling agent (0.5% oww Albegal A, Ciba-Geigy), typical of those used in wool dyeing, was also added. After addition of the dye mixture, the liquor was heated to its boiling point at 2° C./min, where it was maintained for 30 minutes. The liquor was cooled to 75° C. and the sample rinsed and dried. In contrast to the complete dyebath exhaustion obtained on the pretreated wool at 90° C. it was apparent that a much lower level of exhaustion was obtained by the conventional method at the boil.

EXAMPLE 2

A sample of scoured loose wool (44 gm) was treated at a liquor ratio of 10:1 for 30 minutes at 40° C. with a solution containing 0.5 g/l of the compound of the formula.

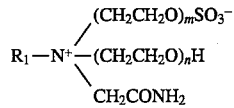

Where R is a hydrocarbon radical containing 18 carbon atoms; and m+n=7.

The solution was adjusted to pH 8 to 8.5 with a mixture of sodium carbonate and sodium bicarbonate.

Following the treatment, the liquor was discarded and the sample dyed at 90° C. from a fresh bath at a liquor:goods ratio of 10:1, by the method described in Example 1. The liquor was free from colour at the end of the dyeing cycle, indicating complete exhaustion of the dyes.

A sample of the scoured loose wool was dyed, at the boil and a liquor:goods ratio of 10:1, by the method described in Example 1. The liquor was free from colour at the end of the dyeing cycle, indicating a lower exhaustion of dyes compared with the above dyeing carried out according to the method of the present invention.

Furthermore, comparison of the wool dyed at 90° C. according to the method of the present invention with the sample dyed by the conventional method at the boil, showed the former to be greatly superior with respect to coverage of tippiness.

EXAMPLE 3

A sample of wool worsted fabric (25 g) was treated by the method described in Example 1. Following the treatment, the liquor was discarded and the sample dyed from a fresh bath. The dyeing method used was as described in Example 1, except that the dyebath was heated to the boil, instead of to 90° C. The dyeing time at the boil was 30 minutes.

A control sample was dyed from a bath containing 0.5% oww Albegal A, as described in Example 1.

Comparison of the two dyebaths at the end of the dyeing cycle showed the exhaustion obtained at the boil on the wool pretreated according to the present invention to be superior to the exhaustion obtained by the usual method at the boil, in the presence of Albegal A.

EXAMPLE 4

A sample of scoured loose wool (44 g) was treated by the method described in Example 2. Following the treatment, the liquor was discarded and the sample dyed from a fresh bath at a liquor:goods ratio of 10:1. The dyeing method used was as described in Example 1, except that the dyebath was heated to the boil, instead of to 90° C. The dyeing time at the boil was 15 minutes.

A control sample was dyed as described in Example 1.

Comparison of the two dyebaths at the end of the dyeing cycle showed the exhaustion obtained at the boil on the wool pretreated according to the present invention to be superior to the exhaustion obtained by the usual method at the boil, in the presence of Albegal A. Furthermore, comparison of the wool pretreated according to the method of the present invention and dyed at the boil with the untreated wool dyed in the presence of Albegal A, showed the former to be superior with respect to coverage of tippiness.

EXAMPLE 5

Two samples of wool fabric were treated separately, at pH 8 to 8.5 for 30 minutes at 40° C., by the methods described in Examples 1 and 2.

Following the treatment, the liquors were discarded and the fabrics dyed separately from a fresh bath. The method used was as described in Example 1, except that 0.25% oww of the commercial moth-proofing agent, Perigen (Wellcombe) was added to the dyebath when the liquor was at 40° C. A dyeing time of 30 minutes at 90° C. was used.

Control dyeings were also carried out at the boil in the presence of various concentrations of the levelling agents shown in Table 1. These proprietary agents are representative of the types commonly used in wool dyeing. These dyebaths also contained 0.25% oww Perigen.

Samples of the following liquors from each dyeing were analysed for the active component of the moth-proofing agent (a synthetic pyrethroid); (a) the dyebath after cooling to 75° C. but before removal of the wool; (b) the liquor used to rime the wool after discarding the dyebath. The results are set out in Table 1.

TABLE 1

Concentration of moth-proofing agent in exhausted dyebath and rinse liquors

| | CONC. MOTH-PROOFING AGENT (ppb) EXHAUSTED: | |
|---|---|---|
| | Dye Liquor (a) | Rinse Liquor (b) |
| (A) Conventional Method | | |
| Albegal A (i) (0.5% oww) | 674 | 87 |
| Albegal A (1.0% oww) | 2440 | 223 |
| Avolan UL75 (ii) (0.5% oww) | 1200 | 164 |
| Avolan UL75 (1.0% oww) | 2425 | 300 |
| Lyogen UL (iii) (1.0% oww) | 2710 | 217 |

TABLE 1-continued

Concentration of moth-proofing agent in exhausted dyebath and rinse liquors

|  | CONC. MOTH-PROOFING AGENT (ppb) EXHAUSTED: | |
| --- | --- | --- |
|  | Dye Liquor (a) | Rinse Liquor (b) |
| (B) With Pretreatment According to the Invention | | |
| As Example 1 | 69 | 138 |
| As Example 2 | 34 | 38 |

(i) Ciba-Geigy
(ii) Bayer
(iii) Sandoz

The results in Table 1 clearly demonstrate the superior exhaustion of moth-proofing agent obtained by the new method, compared with the normal methods used to dye wool.

EXAMPLE 6

A range of alkoxylated hydroxysulphobetaines were prepared by the following method:

In each case, epichlorohydrin (2,3epoxy-1-chloropropane) (0.1 mole) was reacted with an ethoxylated amine (0.1 mole), of general structure:

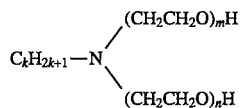

in a mixture of 1,2 propane diol (0.2 mole) and water (0.2 mole). The reaction mixture was maintained at 40° C. for three hours, during which time the pH was kept at 8 by the progressive addition of 2N hydrochloric acid (0.1 mole). Stirring was continued for a further two hours at 40° C., and then 0.1 mole of sodium sulphite was added. The temperature was increased to 100° C., where it was maintained for six hours. The reaction product was a compound with the following general structure:

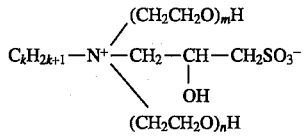

In separate preparations, this method was employed to produce the following specific products:

(i) k=18, m+n=10
(ii) k=16, m+n=15
(iii) k=17, m+n=5

EXAMPLE 7

Samples of the scoured loose wool were treated, at a liquor rate of 10:1 and pH 8 to 8.5 as described in Example 2, with a solution containing 0.5 g/l of the product of (i) above made in accordance with Example 6; i.e:

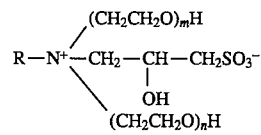

Where R is a hydrocarbon radical containing 18 carbon atoms; and m+n=10.

Following the treatment, the liquor was discarded and the wool dyed from a fresh bath as described in Example 2, except that the dye mixture was replaced with 0.016% oww Neutrichrome Bordeaux S-3B (Crompton and Knowles), 0.027% oww Neutrichrome Grey SBJ and 0.0068% oww Coomassie Blue B (ICI). At the end of the dyeing cycle the liquor was completely clear, indicating complete exhaustion of the dyes.

A sample of the scoured wool was dyed at the boil, at a liquor:goods ratio of 10:1 by the method described in Example 1, except that 1.0% oww of Albegal A was added to the dyebath, instead of 0.5% oww. At the end of the dyeing cycle, visual examination of the dyebath showed the presence of residual dyestuff, indicating a much lower exhaustion of dye compared with the above dyeing at 90° C. on pretreated wool. Comparison of the sample of wool dyed at 90° C. according to the method of the present invention, with that dyed by the conventional method at the boil showed the former to be greatly superior with respect to coverage of tippiness.

EXAMPLE 8

Samples of scoured loose wool were treated as described in Example 7 with 0.5% on mass of fibre of the compound (ii) above made in accordance with Example 6, i.e. the structure illustrated in Example 7, where R is a hydrocarbon radical containing 16 carbon atoms; and m+n=15. Following the treatment, the liquor was discarded and the wool dyed from a fresh bath as described in Example 2, except that the dye mixture was replaced with 0.016% oww Neutrichrome Bordeaux S-3B (Crompton and Knowles), 0.027% oww Neutrichrome Grey SBJ and 0.0068% oww Coomassie Blue B (ICI). At the end of the dyeing cycle the liquor was completely clear, indicating complete exhaustion of the dyes.

A sample of the scoured wool was dyed at the boil, at a liquor:goods ratio of 10:1 by the method described in Example 1, except that 1.0% oww of Albegal A was added to the dyebath, instead of 0.5% oww. At the end of the dyeing cycle, visual examination of the dyebath showed the presence of residual dyestuff, indicating a much lower exhaustion of dye compared with the above dyeing at 90° C. on pretreated wool. Comparison of the sample of wool dyed at 90° C. according to the method of the present invention, with that dyed by the conventional method at the boil showed the former to be greatly superior with respect to coverage of tippiness.

EXAMPLE 9

Samples of scoured loose wool were treated as described in Example 7 with 0.5% on mass of fibre of the compound (iii) above made in accordance with Example 6, i.e. the structure illustrated in Example 7, where R is a hydrocarbon radical containing 17 carbon atoms; and m+n=5. Following the treatment, the liquor was discarded and the wool dyed from a fresh bath as described in Example 2, except that the dye mixture was replaced with 0.016% oww Neutrichrome Bordeaux S-3B (Crompton and Knowles), 0.027% oww Neutrichrome Grey SBJ and 0.0068% oww Coomassie Blue B (ICI). At the end of the dyeing cycle the liquor was completely clear, indicating complete exhaustion of the dyes.

A sample of the scoured wool was dyed at the boil, at a liquor:goods ratio of 10:1 by the method described in Example 1, except that 1.0% oww of Albegal A was added to the dyebath, instead of 0.5% oww. At the end of the dyeing cycle, visual examination of the dyebath showed the presence of residual dyestuff, indicating a much lower exhaustion of dye compared with the above dyeing at 90° C. on pretreated wool. Comparison of the sample of wool dyed at 90° C. according to the method of the present invention, with that dyed by the conventional method at the boil showed the former to be greatly superior with respect to coverage of tippiness.

EXAMPLE 10

A sample of scoured loose wool was treated, at a liquor:wool ratio of 10:1 and pH 8, for 30 minutes at 40° C., with 0.2% oww of the product (50% active) described in Example 7 above. Following the pretreatment, the liquor was acidified to pH 4.5, with formic acid, and the permethrin-containing insect-proofing agent, Pythrin WB (Rudolf Chemicals) (0.9% oww of a 10% active product) was added. Following addition of the dyestuff Neutrichrome Bordeaux S-3B (0.2% oww), the dyebath was heated to 90° C. over 25 minutes, where it was held for a further 30 minutes. The dye liquor was discarded and the wool was rinsed. Samples of the exhausted dyebath and the rinse liquor were retained and analysed for permethrin.

Visual examination showed that the dyestuff was completely exhausted onto the wool. Furthermore, the coverage of tippiness was greatly superior to that obtained on an untreated wool sample also dyed with 0.2% oww of Neutrichrome Bordeaux S-3B.

The concentrations of permethrin in the dyebath and rinse liquor were 180 ppb and 270 ppb respectively. These values represent a percentage exhaustion of 99.5% of the amount of permethrin added to the dyebath.

In marked contrast to the above figures, a sample dyed in the presence of a conventional levelling agent (Avolan UL75, Bayer), at the boil, gave concentrations of permethrin in the exhausted dyebath greater than 10000 ppb; this represents an exhaustion level of less than 90% of the amount of permethrin added to the dyebath.

EXAMPLE 11

A sample of scoured loose wool was treated, at a liquor:wool ratio of 10:1 and pH 7.5, for 15 minutes at 40° C., with 0.2% oww of the product described in Example 7. Following the pretreatment, the liquor was acidified with formic acid to pH 4.5 and then 0.5% oww of the dye Lanaset Red G (Ciba-Geigy) was added. The dyebath was heated to the boil over 45 minutes, where it was held for a further 15 minutes, after which time the dyestuff had exhausted completely onto the wool.

EXAMPLE 12

A sample of a pure wool fabric was treated at a liquor:wool ratio of 20:1 and pH 7.5, for 20 minutes at 40° C., with 0.4% oww of the product described in the Example 11. The liquor was then adjusted to pH 4.5 with formic acid and the dyestuffs Erio Red 2B (1.8% oww) and Erio Blue BGL (0.8% oww) (Ciba-Geigy) were added. The dyebath was heated to the boil over 45 minutes, where it was held for a further ten minutes, after which time exhaustion of the dyestuffs was complete.

EXAMPLE 13

A sample of loose wool was pretreated and dyed as described in Example 11, except that 0.9% oww of the commercial moth-proofing formulation Perigen EC (Wellcombe) was added to the dyebath before the temperature was raised. (Perigen EC contains 10% (mass/volume) of the synthetic pyrethroid, permethrin). The concentrations of permethrin in the exhausted dyebath and rinse liquor were 310 ppb and 230 ppb respectively.

In contrast to these results, a sample dyed at the boil in the presence of 1% oww of a conventional levelling agent (Albegal A, Ciba-Geigy) gave a concentration of permethrin in the exhausted dyebath greater than 7000 ppb. Furthermore, the wool sample dyed by the method of the present invention showed superior coverage of "tippiness" compared with the sample dyed in the presence of the conventional dye levelling agent.

We claim:

1. A method of applying dye to keratin fibres comprising pretreating the fibres by contacting them with an alkaline solution of an amphoteric surfactant, and thereafter applying dye to the pretreated fibres from a dyeing solution which is substantially deficient of surfactant-type levelling agents but includes one or more insect-proofing agents, wherein said amphoteric surfactant comprises an alkoxylated hydroxysulphobetaine of formula:

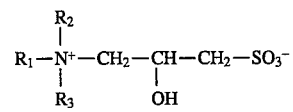

where:

$R_1$ is a hydrocarbon group selected from the range $C_{12}H_{25}$ up to $C_{21}H_{43}$; and $R_2$ and $R_3$ are poly(alkylene oxide) groups, each having n alkylene oxide units, where $3 \leq n \leq 21$.

2. A method according to claim 1, wherein the fibres are separated from said alkaline solution before being contacted with said dyeing solution.

3. A method according to claim 1 or 2, wherein said alkaline solution has a pH greater than 7 but not greater than 11.

4. A method according to claim 3, wherein said pH is in the range of 8.0 to 8.5.

5. A method according to claim 1, wherein said amphoteric surfactant is present in the amount of at least 0.1% oww with respect to the fibres.

6. A method according to claim 1, wherein said pretreatment is carried out at a temperature in the range of 5° to 100° C.

7. A method according to claim 6, wherein said pretreatment is carried out at a temperature in the range of 20° to 50° C.

8. A method according to claim 1, wherein said pretreatment is carried out for a period in the range of 10 to 60 minutes.

9. A method of according to claim 1, wherein said alkaline solution is an aqueous solution.

10. A method according to claim 1, wherein said dyeing solution is aqueous and said dye is a water soluble dye.

11. A method according to claim 10, wherein said dyeing solution is acidic and said dye is a water soluble dye normally used for the coloration of keratin fibres.

12. A method according to claim 1, wherein $R_2$ and $R_3$ are each polyethylene or polypropylene oxide groups or a mixture of polyethylene and polypropylene oxide groups.

13. A method according to claim 1 or 12, wherein each of $R_2$ and $R_3$ respectively contains $n_1$ and $n_2$ alkylene oxide units and $6 \leq n_1 + n_2 \leq 21$.

14. A method according to claim 1, wherein said pretreatment and said dye applying steps are effected in a single bath liquor which is initially said alkaline solution for said pretreatment step and then is converted to said dyeing solution for the dye applying step, said amphoteric surfactant being selected so as to be substantially exhausted from the bath liquor before said conversion of the bath.

15. A method according to claim 14, wherein said conversion of the bath comprises changing the bath from an alkaline solution to an acidic solution and then adding said dye.

16. A method according to claim 1, wherein the fibres are wool fibres.

17. A method according to claim 16, wherein the wool fibres are pretreated while raw scoured fibres.

18. A method according to claim 1, wherein the fibres are in a fabric.

19. A method according to claim 1, wherein the fibres are incorporated into a fabric between said pretreatment and said application of dye to the fibres.

20. A method according to claim 16, wherein the wool fibres are pretreated while in a yarn.

21. A method according to claim 13, wherein $R_1$ has 18 carbon atoms, $R_2$ and $R_3$ are polyethylene oxide groups, and $n_1 + n_2 = 10$.

22. A method of applying dye to keratin fibres comprising pretreating the fibres by contacting them with a bath liquor comprising an alkaline solution of an amphoteric surfactant, and thereafter adding dye to the bath liquor and applying the dye to the fibres from said bath liquor, wherein said amphoteric surfactant comprises an alkoxylated hydroxysulphobetaine of general structure:

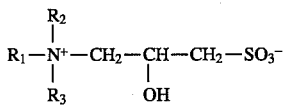

where:
$R_1$ is a hydrocarbon group selected from the range $C_{12}H_{25}$ up to $C_{21}H_{43}$;
$R_2$ and $R_3$ are poly(alkylene oxide) groups, each having n alkylene oxide units, where $3 \leq n \leq 21$;
wherein said bath liquor is substantially deficient of any surfactant-type levelling agents other than alkoxylated hydroxysulphobetaine of said structure; and
wherein said bath liquor is a single bath liquor which is initially said alkaline solution for said pretreating step and then is converted to a dyeing solution for the dye applying step by said adding of dye to the bath liquor.

23. A method according to claim 22, wherein said conversion includes, after the contacting of the fibres with the alkaline bath liquor and before the dye is added, converting said bath liquor from an alkaline solution to an acidic solution.

24. A method according to claim 22 or 23, wherein $R_2$ and $R_3$ are each polyethylene or polypropylene oxide groups or a mixture of polyethylene and polypropylene oxide units.

25. A method according to claim 22 or 23, wherein $R_2$ and $R_3$ respectively contains $n_1$ and $n_2$ alkylene oxide units and $6 \leq n_1 + n_2 \leq 21$.

26. A method according to claim 25, wherein $R_1$ has 18 carbon atoms, $R_2$ and $R_3$ are polyethylene oxide groups, and $n_1 + n_2 = 10$.

27. A method according to claim 22, wherein said bath liquor includes one or more insect-proofing agents.

28. A method according to claim 22 or 27 wherein said amphoteric surfactant is selected so as to be substantially exhausted from the bath liquor before said conversion.

29. A method according to claim 22 or 23, wherein said alkaline solution has a pH greater than 7 but not greater than 11.

30. A method according to claim 29, wherein said pH is in the range of 8.0 to 8.5.

31. A method according to claim 22 or 23, wherein said amphoteric surfactant is present in the amount of at least 0.1% oww with respect to the fibres.

32. A method according to claim 22 or 23, wherein said pretreatment is carried out at a temperature in the range of 5° to 100° C.

33. A method according to claim 32, wherein said pretreatment is carried out at a temperature in the range of 20° to 50° C.

34. A method according to claim 22 or 23, wherein said pretreatment is carried out for a period in the range of 10 to 60 minutes.

35. A method according to claim 22 or 23, wherein said bath liquor is an aqueous solution.

36. A method according to claim 22 or 23, wherein said dye is a water soluble dye.

37. A method according to claim 22 or 23, wherein said dyeing solution is acidic and said dye is a water soluble dye normally used for the coloration of keratin fibres.

38. A method according to claim 22 or 23, wherein the fibres are wool fibres.

39. A method according to claim 38, wherein the wool fibres are raw scoured fibres.

40. A method according to claim 38, wherein the wool fibres are in a yarn.

41. A method according to claim 22 or 23, wherein the fibres are in a fabric.

42. A method of applying dye to keratin fibres comprising contacting said fibres with a dyebath liquor including one or more insect-proofing agents and an amphoteric surfactant levelling agent which comprises an alkoxylated hydroxysulphobetaine of general structure:

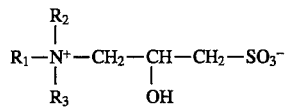

where:
$R_1$ is a hydrocarbon group selected from the range $C_{12}H_{25}$ up to $C_{21}H_{43}$;
$R_2$ and $R_3$ are poly(alkylene oxide) groups, each having n alkylene oxide units, where $3 \leq n \leq 21$;
wherein said dyebath liquor is substantially deficient of any surfactant-type levelling agents other than alkoxylated hydroxysulphobetaine of said general structure.

* * * * *